United States Patent [19]

Alker et al.

[11] Patent Number: 5,486,527
[45] Date of Patent: Jan. 23, 1996

[54] ANTICHOLINERGIC AGENTS

[75] Inventors: David Alker, Birchington; Peter E. Cross, Canterbury, both of England

[73] Assignee: Pfizer Inc., New York, N.Y.

[21] Appl. No.: 282,191

[22] Filed: Jul. 28, 1994

Related U.S. Application Data

[63] Continuation of Ser. No. 877,170, Jun. 29, 1992, abandoned.

[30] Foreign Application Priority Data

Jan. 6, 1990 [GB] United Kingdom ............... 9000305

[51] Int. Cl.$^6$ .............. A61K 31/445; C07D 405/06; C07D 405/12
[52] U.S. Cl. .............. 514/321; 514/252; 514/317; 514/318; 514/319; 514/320; 514/326; 514/343; 514/408; 514/422; 514/428; 544/229; 544/336; 546/193; 546/197; 548/526
[58] Field of Search .............. 544/336, 229; 546/192, 193, 194, 195, 196, 197, 205, 213, 236, 241, 281, 283, 14; 548/406, 525, 526, 527, 570, 575, 578, 579, 577; 514/317, 318, 319, 320, 321, 326, 343, 252, 408, 422, 428

[56] References Cited

U.S. PATENT DOCUMENTS

| | | | |
|---|---|---|---|
| 4,540,780 | 9/1985 | Downs | 544/360 |
| 5,096,890 | 3/1992 | Cross | 546/275 |
| 5,233,053 | 8/1993 | Cross | 548/568 |

OTHER PUBLICATIONS

Kalsner "Trends in autonomic pharmacology" Tayer & Francis pp. 17–19, 28–31 (1985).

Primary Examiner—Ceila Chang
Attorney, Agent, or Firm—Peter C. Richardson; Gezina Holtrust; B. Timothy Creagan

[57] ABSTRACT

Selective muscarinic receptor antagonists of formula (I):

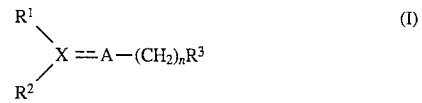

wherein $R^1$ and $R^2$ are both optionally substituted phenyl, the broken line is an optional bond, X is >COH—, >SiOH— or CH— when the double bond is absent or is >C= when the double bond is present, X being attached to a carbon atom of A, A is selected from certain piperidine and pyrrolidine groups, n is 1 to 3 and $R^3$ is optionally substituted phenyl or thienyl, pyridyl or pyrazinyl.

7 Claims, No Drawings

ANTICHOLINERGIC AGENTS

This is a continuation of application Ser. No. 07/877,170, filed on Jun. 29, 1992, now abandoned, which is the national stage of PCT/EP90/02262 filed Dec. 18, 1990.

BACKGROUND OF THE INVENTION

This invention relates to certain disubstituted piperidine and pyrrolidine derivatives as selective muscarinic receptor antagonists.

GB-780,027 discloses, amongst other compounds, 3-(benzhydryloxy)- and 3-(xanthyloxy)-N-aralkylpiperidines as oxytocic agents, being devoid of antispasmodic activity at the therapeutic doses employed. No N-phenethyl substituted examples were synthesised or exemplified within the scope.

U.S. Pat. No. 2,974,146 provides N-aralkyl-3-piperidyl benzhydryl ethers having activity as sedatives and in prolonging the hypnotic effect of barbiturates, with only the corresponding quaternary ammonium salts being stated to possess gastro-intestinal antispasmodic activity. Although N-phenethyl-3-piperidyl benzhydryl ether is listed as "a specific compound provided by the invention", no preparative details or pharmacological data are presented and it is clear that the compound was never actually made.

SUMMARY OF THE INVENTION

U.S. Pat. No. 4,632,925 describes N-substituted diphenylpiperidines which exhibit insulin-lowering activity.

It has now unexpectedly been discovered that the substituted piperidine and pyrrolidine derivatives provided by the present invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesphageal achalasia and chronic obstructive airways disease.

According to one aspect of the invention, there are provided compounds of the formula (I):

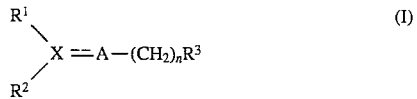

and their pharmaceutically acceptable salts, wherein $R^1$ and $R^2$ are the same or different and each is phenyl which is unsubstituted or substituted by at least one group selected from $C_1$–$C_4$ alkyl and halo, the broken line represents an optional double bond and X is >COH, >SiOH— or >CH— when said double bond is absent or is >C= when said double bond is present, X being attached to a carbon atom of A, A is

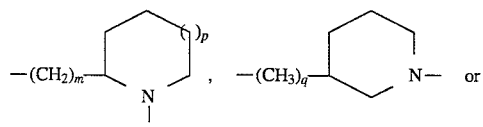

when said double bond is absent or A is

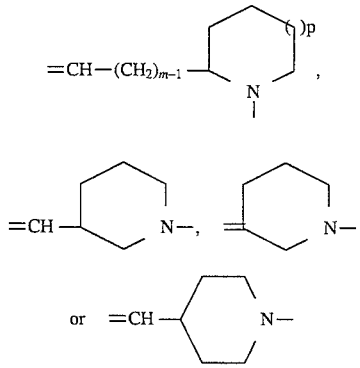

when said double bond is present n is from 1 to 3,
m is 1 or 2,
p is 0 or 1,
q is 0 or 1
$R^3$ is

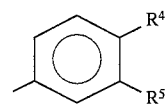

or Het, $R^4$ and $R^5$ are each independently H, $C_1$–$C_4$ alkyl, $C_1$–$C_4$ alkoxy or $(CH_2)_r$OH wherein r is 0, 1 or 2, or $R^4$ and $R^5$ together form a —Y—$(CH_2)_s$—Z— group wherein Y and Z are independently —O— or —$CH_2$— and s is 1, 2 or 3, and Het is thienyl, pyridyl or pyrazinyl, with the provisos that when q is O or A is

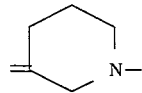

then n is 2 or 3, and that when A is

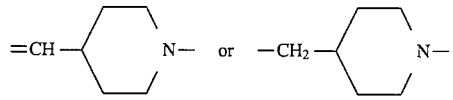

then $R^3$ is not Het.

In the above definitions "thienyl" includes 2- and 3-thienyl and pyridyl includes 2-, 3- and 4-pyridyl. "Halo" means F, Cl, Br or I. Alkyl and alkoxy groups of 3 or more carbon atoms may be straight or branched-chain. The preferred alkyl and alkoxy groups are methyl, ethyl, methoxy and ethoxy.

$R^1$ and $R^2$ may be unsubstituted phenyl. X is preferably >C(OH)—. Preferred examples of $R^3$ are pyridyl, 2,3-dihydrobenzofuranyl, 3,4-methylenedioxyphenyl, tolyl, methoxyphenyl and hydroxymethylphenyl.

A particularly preferred compound is 3-(diphenylhydroxymethyl)-1-(3,4-methylenedioxyphenethyl)piperidine.

The compounds of the formula (I) contain at least one asymmetric centre and will therefore exist as a pair of enantiomers or diastereomeric pairs of enantiomers. Such enantiomers or diastereomeric pairs of enantiomers may be resolved by physical methods, e.g. by fractional recrystallisation, chromatography or H.P.L.C. of a racemic mixture of the compound of the formula (I), or of a suitable salt or derivative thereof. Most preferably, the individual enantiomers of the compounds of the formula (I) containing one asymmetric centre are prepared from optically pure intermediates.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the solution.

DETAILED DESCRIPTION OF THE INVENTION

The compounds of the formula (I) can be prepared by a number of routes, including the following:

Route A

This can be illustrated as follows:

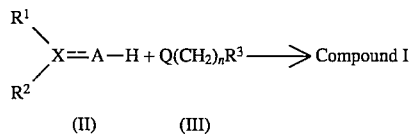

(II)      (III)

$R^1$, $R^2$, A, X, n and $R^3$ are as defined for formula (I) and Q is a leaving group, e.g. Br, Cl, I, $C_1$–$C_4$ alkanesulphonyloxy (e.g. methanesulphonyloxy), benzenesulphonyloxy, toluenesulphonyloxy (e.g. p-toluenesulphonyloxy) or trifluoromethanesulphonyloxy. Preferably, Q is Cl, Br, I or methanesulphonyloxy. In formula (II) the hydrogen atom shown is attached to the nitrogen atom of A.

The reaction is preferably carried out in the presence of an acid acceptor such as sodium or potassium carbonate, sodium bicarbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux. Iodo is generally the most suitable leaving group but since the starting materials (III) are generally most conveniently available as chlorides or bromides, the reaction is often most suitably carried out using the compound (III) as a chloride or bromide but in the presence of an iodide such as sodium or potassium iodide. In the preferred technique, the compounds (II) and (III), (III) being in bromide or chloride form, are refluxed together in acetonitrile in the presence of sodium carbonate and sodium iodide. The product (I) can be isolated and purified conventionally.

The starting materials of the formula (II) can be obtained by conventional procedures such as those described in the Preparations below. The starting materials of the formula (III) are in general known compounds which can be prepared by conventional techniques.

The preparation of the novel starting materials of the formula (III) used in the Examples is described in the following Preparations section.

Route B

This route is useful for preparing compounds in which n is 2 and $R^3$ is 2- or 4-pyridyl or pyrazinyl and can be described as follows:

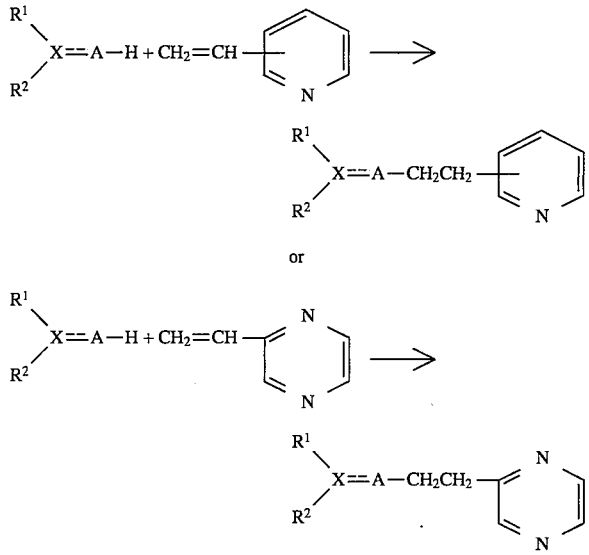

$R^1$, $R^2$, A and X are as defined for formula (I). Clearly the vinyl group must be attached to the 2- or 4-position of the pyridine ring.

The reaction is typically carried out with heating at up to 160° C., preferably 80° to 140° C., in a suitable organic solvent, e.g. 1-butanol. The use of a basic (preferably a strong base which is soluble in an organic solvent such as N-benzyltrimethylammonium hydroxide ["Triton B"-Trade Mark] or acidic (preferably a $C_1$–$C_4$ alkanoic acid) catalyst is useful. The preferred procedure is to reflux the reactants in an organic solvent in the presence of a basic catalyst such as "Triton B".

Route C

This route may be used when $R^1$ and $R^2$ are phenyl and X is >C(OH)— and may be illustrated as follows:

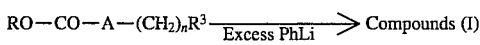

wherein R is a $C_1$–$C_4$ alkyl group such as ethyl. In this process a carboxylate of the appropriate piperidine or pyrrolidine derivative is allowed to react with excess phenyllithium to convert the RO—CO— group to a $Ph_2C(OH)$— group. The reaction may be conducted by adding the phenyllithium to the carboxylate in a suitable solvent such as diethyl ether at low temperature, allowing the mixture to warm to room temperature, quenching the remaining phenyllithium with water and extracting the desired compound of formula (I) with a suitable organic solvent. The carboxylate starting compounds may be prepared as described in the Preparations below.

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiologist salt solution containing the lowest dose of the test compound. The test compound is allowed is to equilibrate with the tissue for 20 minutes and the agonist dose-response curve is repeated until the maximum response is obtained. The organ bath is drained and refilled with physiologist salt solution containing the second concentration of test compound and the above procedure is repeated. Typically four concentrations of the test compound are evaluated on each tissue.

The concentration of the test compound which causes a doubling of the agonist concentration required to produce the original response is determined ($pA_2$ value—Arunlakshana and Schild (1959), Brit. J. Pharmacol., 14, 48–58). Using the above analytical techniques, tissue selectivity for muscarinic receptor antagonists is determined.

Activity against agonist induced bronchoconstriction, gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse on either intravenous or intraperitoneal administration. Thus, the dose to cause a doubling of pupil size is determined as well as the dose to inhibit by 50% the salivation and tremor responses to intravenous oxotremorine.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for any average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with age, weight and response of the particular patient. The above dosages are exemplary of the average case but there can, of course, be individual instances where higher or lower dosage ranges are merited, and such are within the scope of this invention.

For human use, the compounds of formula (I) can be administered alone, but will generally be administered in admixture with a pharmaceutical carrier selected with regard to the intended route of administration and standard pharmaceutical practice. For example, they may be administered orally in the form of tablets containing such excipients as starch of lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for examples, enough salts or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone smooth muscle, such as irritable bowel syndrome, diverticular disease, urinary incontinence, oesophageal achalasia and chronic obstructive airways disease.

The following Examples, in which all temperatures are in °C., illustrate the invention.

EXAMPLES 1

1-[(2,-(2,3-Dihydro-5-benzofuranyl)ethyl]-3-(diphenylhydroxymethyl)-piperidine

A mixture of 3-(diphenylhydroxymethyl)piperidine (135 mg, 0.50 mmol) (see J. Org. Chem., 4084, 26, 1961 for preparation), 5-(2-bromoethyl)-2,3-dihydrobenzofuran (115 mg, 0.50 mmol), sodium carbonate (0.50 g) and sodium iodide (50 mg) in acetonitrile (20 ml) was heated under reflux for 16 hour, filtered and evaporated. The residue was partitioned between ethyl acetate and water and the organic layer was washed with water, dried over magnesium sulphate and evaporated. The residue was purified by chromatography on $SiO_2$ (6 g) using dichloromethane plus 0–20% ethyl acetate as eluant. Appropriate fractions were combined and evaporated to give the title compound (110 mg) as a colourless oil which was characterised as a hemihydrate.

Analysis %: Found: C,79.7; H,7.5; N,3.1; $C_{28}H_{31}NO_2.0.5H_2$ requires: C,79.6; H,7.6; N,3.3.

EXAMPLES 2–9

The compounds of Table 1 were prepared by the method of Example 1 by reacting the appropriate piperidine derivative with the appropriate alkylating agent $Q(CH_2)_nR^3$ and were obtained in the form shown. The starting materials for Examples 4 and 5 were each used as their hydrochloride salts.

TABLE 1

$$\text{Ph}_2 X = \text{(cyclohexane ring)} - N-(CH_2)_n R^3$$

| Example No | X | R | Q | n | Form characterised | Analysis % (Theoretical in brackets) C | H | N |
|---|---|---|---|---|---|---|---|---|
| 2 | \C(OH)— (Ph,Ph) | benzodioxole | Br | 2 | hemihydrate m.p. 95–96° C. | 76.3 (76.4 | 6.9 7.1 | 3.4 3.3) |
| 3 | \C(OH)—CH₂— | benzodioxole | Br | 2 | hydrate, gum | 75.1 (75.1 | 7.0 7.4 | 3.2 3.1) |
| 4 | \C= | benzodioxole | Br | 2 | gum | 81.9 (81.6 | 6.9 6.8 | 3.4 3.5) |
| 5 | \CH— | benzodioxole | Br | 2 | m.p. 92–94° C. | 81.0 (81.2 | 7.30 7.3 | 3.7 3.5) |
| 6 | \C(OH)— | phenyl-CH₂OH | Br | 2 | hemihydrate, m.p. 175–178° C. | 78.9 (79.0 | 7.8 7.7 | 3.3 3.4) |
| 7 | \C(OH)— | phenyl-Me | Br | 2 | hydrate m.p. 108–112° C. | 79.6 (80.4 | 7.8 8.2 | 3.4 3.5) |
| 8 | \C(OH)—CH₂— | phenyl-OMe | Br | 2 | 0.25 hydrate, gum | 80.1 (80.1 | 8.0 8.0 | 3.35 3.35) |
| 9 | \C(OH)—CH₂— | benzodioxole | Cl | 1 | 0.67 hydrate foam | 75.7 (75.8 | 7.0 7.1 | 3.5 3.3) |

EXAMPLES 10

3-(Diphenylhydroxymethyl)-1-[2-(2-pyridyl)ethyl]piperidine

A mixture of 3-(diphenylhydroxymethyl)piperidine (267 mg, 1.0 mmol), 2-vinylpyridine (0.32 g, 3.0 mol) and Triton B (3 drops) in 1-butanol (10 ml) was heated under reflux for 18 hours, diluted with water and ethyl acetate and the layers separated. The organic layer was washed with water, dried over magnesium sulphate and evaporated. The residue was twice taken up in toluene and evaporated and it was then purified by chromatography on $SiO_2$ using dichloromethane plus 0–5% methanol as eluant. Appropriate fractions were combined and evaporated to give the title compound (80 mg) as a pale brown oil which was characterised containing 0.25 equivalents of water.

Analysis %: Found: C, 79.7; H,7.4; N7.4; $C_{25}H_{28}N_2O.0.25H_2O$ requires: C,79.7; H,7.6; N,7.4.

EXAMPLE 11

1-[2-(2,3-Diphydro-5-benzofuranyl)ethyl]-4-(2,2-diphenyl-2-hydroxyethyl)piperidine A 1.9M solution of phenyllithium (1.0 ml, 1.9 mmol) was added dropwise over 10 minutes to a stirred solution of ethyl 1-[2-(2,3-dihydro-5-benzofuranyl)ethyl]piperidine-4-acetate (130 mg, 0.40 mmol) in ether (10 ml) with cooling in an acetone/$CO_2$ bath. The mixture was stirred at−70° C. for 1 hour, allowed to warm to room temperature and stirred for 16 hours. The mixture was quenched cautiously with water and extracted into ethyl acetate. The ethyl acetate extract was washed with water, dried over magnesium sulphate and evaporated. The residue was purified by chromatography on $SiO_2$ using dichloromethane plus 20% ethyl acetate plus 0–5% methanol as eluant. Appropriate fractions were combined and evaporated to give the title compound (100 mg) as a colourless foam which was characterised as a hemihydrate.

Analysis %: Found: C,79.7; H,7.7; N,3.5; $C_{29}H_{33}NO_2.0.5H_2O$ requires: C,79.8; H,7.8; N,3.2.

EXAMPLE 12

4-(2,2-Diphenyl-2-hydroxy)ethyl-1-(3,4-methylenedioxybenzyl)piperidine

The title compound was prepared by the method of Example 11 by reacting phenyllithium with ethyl 1-(3,4-methylenedioxybenzyl)piperidine-4-acetate. The title compound was obtained as a colourless solid, m.p. 142°–145° C., which was characterised containing 0.25 equivalents of water.

Analysis %: Found: C,77.2; H,7.1; N,3.2; $C_{27}H_{29}NO_3.0.25H_2O$ requires: C,77.2; H,7.0; N,3.3.

EXAMPLE 13

3-(Diphenylhydroxymethyl)-1-(4-methoxyphenethyl)piperidine

The title compound was prepared by the method of Example 11 by reacting phenyllithium with ethyl 1-(4-methoxyphenethyl)piperidine-3-carboxylate. The title compound was obtained as a colourless oil.

Analysis %: Found: C,80.3; H,7.7; N,3.5; $C_{27}H_{31}NO_2$ requires: C,80.8; H,7.8; N,3.5.

EXAMPLE 14

3-(2,2-Diphenyl-1-ethenyl)-1-(3,4-methylenedioxyphenethyl)piperidine Hydrochloride A solution of 3-(2,2-diphenyl-2-hydroxyethyl)-1-(3,4-methylenedioxyphenethyl)piperidine hydrate (162 mg) (Example 3) in 2M hydrochloric acid (4.5 ml) was heated at 100° C. for 30 minutes and evaporated to give the title compound as a colourless foam (165 mg, 98%), which was characterised as a hydrate.

Analysis %: Found: C, 72.4; H, 6.7; N, 3.0; $C_{28}H_{29}NO_2.HCl.H_2O$ requires: C, 72.2; H, 6.9; N, 3.0.

EXAMPLE 15

3-(2,2-Diphenylethyl)-1-(3,4-methylenedioxyphenethyl)piperidine

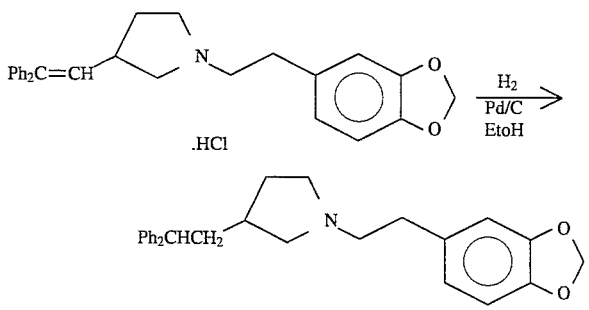

A solution of 3-(2,2-diphenyl-1-ethenyl)-1-(3,4-methylenedioxyphenethyl)piperidine hydrochloride (135 mg) (Example 14) in EtOH (20 ml) was stirred at 40° C. under a hydrogen atmosphere of 45 psi in the presence of 10% palladium on charcoal. The mixture was filtered and the filtrate evaporated. The residue was partitioned between dichloromethane and 2M aqueous sodium hydroxide solution and the organic layer was dried over sodium sulphate and evaporated. The residue was purified by chromatography on silica using dichloromethane plus 2.5% methanol as eluant. Appropriate fractions were combined and evaporated to give the title compound as a colourless oil (60 mg, 50%) which was characterised as a hemihydrate.

Analysis %: Found: C, 79.7; H, 7.4; N, 3.2; $C_{28}H_{31}NO_2.0.5H_2O$ requires: C, 79.6; H, 7.6; N, 3.3.

PREPARATION 1

3-Diphenylmethylenepiperidine Hydrochloride

A mixture of 3-(diphenylhydroxymethyl)piperidine (801 mg, 3.0 mmol) and 2M hydrochloric acid (12 ml) was stirred at 100° C. for 2 hours and evaporated. The residue was triturated with toluene and recrystallised from methanol to give the title compound (730 mg) as a colourless solid, m.p. 236°–237° C.

Analysis %: Found: C,75.3; H,7.1; N,4.6; $C_{18}H_{19}N.HCl$ requires: C,75.6; H,7.0; N,4.9.

PREPARATION 2

3-Diphenylmethylpiperidine Hydrochloride

A solution of 3-diphenylmethylenepiperidine hydrochloride (200 mg, 0.7 mmol) in ethanol (40 ml) was stirred under one atmosphere of hydrogen at 40° C. in the presence of 10% palladium on charcoal (20 mg) for 24 hours and filtered. The filtrate was concentrated to give the title compound (200 mg) as a pale brown gum which was characterised by its $^1$H-NMR spectrum.

$^1$H-NMR ($d_6$-DMSO) δ=8.7–9.1(1H,broad s), 7.0–7.45(10H,m), 2.4–3.8(4H,m), 1.4–1.8(4H,m) and 1.0–1.25(2H,m).

PREPARATION 3

Ethyl 1-(3,4-methylenedioxybenzyl)piperidine-4-acetate

A mixture of ethyl piperidine-4-acetate (0.34 g, 2.0 mmol), 3,4-methylenedioxybenzyl chloride (0.34 g, 2.0 mmol), sodium carbonate (1.0 g) and sodium iodide (0.10 g) in acetonitrile (30 ml) was heated under reflux for 16 hours and evaporated. The residue was partitioned between ethyl acetate and water and the organic layer was washed with water, dried over magnesium sulphate and evaporated. The residue was purified by chromatography on $SiO_2$ using dichloromethane plus 0–20% ethyl acetate as eluant. Appropriate fractions were combined and evaporated to give the title compound (0.52 g) as a colourless oil which was characterised by its $^1$H-NMR spectrum.

$^1$H-NMR (CDCl$_3$) δ=6.87(1H,s), 6.77(2H,s), 5.97(2H,s), 4.13(2H,q,J=7 Hz), 3.41(2H,s), 2.94(2H,d,J=8 Hz), 2.23(2H,d,J=6 Hz), 1.6–2.05(5H,m), 1.2–1.45(2H,m) and 1.25(3H,t,J=7 Hz).

PREPARATION 4

Ethyl 1-[2-(2,3-dihydro-5-benzofuranyl)ethyl]piperidine-4-acetate

This compound was prepared as described in Preparation 3 but using 5-(2-bromoethyl)-2,3-dihydrobenzofuran instead of 3,4-methylenedioxybenzyl chloride. The title compound was obtained as a colourless oil which was characterised by its $^1$H-NMR spectrum.

$^1$H-NMR (CDCl$_3$) δ=7.08(1H,s), 6.95(1H,d,J=8 Hz), 6.74(2H,d,J=8 Hz), 4.58(2H,t,J=7 Hz), 4.16(2H,q,J=7 Hz), 3.21(2H,t,J=7 Hz), 3.03(2H,d,J=8 Hz), 2.5–2.8(4H,m), 2.23(2H,d,J=4 Hz), 2.04(2H,dt,J=8 and 1.5 Hz), 1.6–1.95(2H,m), 1.3–1.5(2H,m) and 1.25(3H,t,J=7 Hz).

PREPARATION 5

3,4-Methylenedioxyphenethyl alcohol 3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%), which was characterised by its $^1$H-NMR spectrum.

$^1$H-NMR (CDCl$_3$) δ=6.69–6.83 (3H,m); 5.98(2H,s); 3.82(2H,dt J=7 and 6 Hz); 2.81(2H,t,J=7 Hz) and 1.44(1H, t, J=6 Hz, exchangeable with D$_2$O).

PREPARATION 6

3,4-Methylenedioxyphenethyl bromide

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 5) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g, 40%), which was characterised by its $^1$H-NMR spectrum.

$^1$H-NMR (CDCl$_3$) δ=6.80(1H,d,J=8 Hz), 6.75(1H,s), 6.71(1H,d,J=8 Hz), 6.00(2H,s), 3.56(2H,t,J=7 Hz) and 3.13 (2H,t,J =7 Hz).

PREPARATION 7

5-(2-Hydroxyethyl)-2,3-dihydrobenzofuran

A solution of (2,3-dihydro-5-benzofuranyl)acetic acid (4.9 g—see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide solution (1.5 ml) and water (4.5 ml). The mixture was filtered and the inorganic salts were washed with ethyl acetate. The filtrate and washings were combined and evaporated to give the title compound as an oil, (3.3 g), which was characterised by its $^1$H-NMR spectrum.

$^1$H-NMR (CDCl$_3$) δ=7.10 (s,1H), 7.00 (d, 1H), 6.75(m, 1H), 4.65–4.55(m,2H), 3.90–3.75(m,2H), 3.30–3.15(m,2H), 2.90–2.80(m,2H) and 1.85–1.75(brs,1H).

PREPARATION 8

5-(2-Bromoethyl)-2,3-dihydrobenzofuran

Phosphorus tribomide (0.37 g) was added to a solution of 5-(2-hydroxyethyl)-2,3-dihydrobenzofuran (0.612 g) (Preparation 7) in carbon tetrachloride (3 ml) and the mixture heated under reflux for 3 hours and partitioned between 10% aqueous sodium carbonate solution (20 ml) and dichloromethane (20 ml). The layers were separated and the aqueous layer was extracted with dichloromethane. The combined dichloromethane extracts were dried (MfSO$_4$) and evaporated to give the title compound (0.584 g) as an oil which crystallised on standing, m.p. 60°–62° C., and which was characterised by its $^1$H-NMR spectrum.

$^1$H NMR (CDCl$_3$) δ=7.10(s,1H), 7.00–6.95(d,1H), 6.80–6.70(d,1H), 4.65–4.55(t,2H), 3.60–3.50(t,2H), 3.25–3.15(t,2H) and 3.15–3.10(t,2H).

PREPARATION 9

Ethyl 1-(4-methoxyphenethyl)piperidine-3-carboxylate

This compound was prepared as described in Preparation 3 using ethyl piperidine-3-carboxylate and 4-methoxyphenethyl bromide as reagents. The title compound was obtained as a colourless oil.

Analysis %: Found: C,69.2; H,8.3; N,4.8; C$_{17}$H$_{25}$NO$_3$ requires: C,70.1; H,8.6; N,4.8.

The following compounds may be prepared by methods described in the respective publications given below:

| | |
|---|---|
| 3-(Diphenylhydroxymethyl)-piperidine | Journal of Organic Chemistry, 4084, 26, (1961). |
| 3-(2,2-diphenyl-2-hydroxy)ethyl piperidine | British Patent Specification 765853. |
| Ethyl piperidine-4-acetate | Journal of American Chemical Society, 6249, 75, (1953). |

It will be appreciated from the foregoing that what we will claim may include the following:

(1) The compounds of the formula (I) and pharmaceutically acceptable salts thereof;

(2) Processes as described herein for preparing the compounds of the formula (I) and their salts;

(3) Pharmaceutical compositions comprising a compound of the formula (I) or a pharmaceutically acceptable salt thereof, and a pharmaceutically acceptable diluent or carrier;

(4) Any novel intermediates described herein;

(5) A compound of the formula (I), or a pharmaceutically acceptable salt thereof for use as a medicament.

(6) The use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

We claim:

1. A compound of the formula (I):

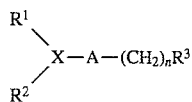 (I)

or a pharmaceutically acceptable salt thereof, wherein $R^1$ and $R^2$ are the same or different and each is phenyl which is unsubstituted or substituted by at least one group selected from $C_1$–$C_4$ alkyl and halo, X is

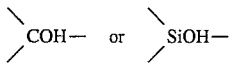

X being attached to a carbon atom of A, A is

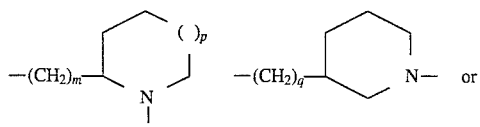

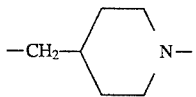

n is from 1 to 3,
m is 1 or 2,
p is 1,
q is 1

$R^3$ is 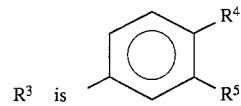

wherein $R^4$ and $R^5$ are taken together to form a —Y—$(CH_2)_s$—Z— group wherein Y and Z are independently —O— or —$CH_2$— and s is 1, 2 or 3.

2. A compound according to claim 1, in which $R^1$ and $R^2$ are both unsubstituted phenyl.

3. A compound according to 2, in which X is >C(OH)—.

4. A compound according to claim 1, in which $R^3$ is, 2,3-dihydro-benzofuranyl,

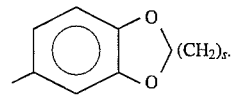

5. A compound according to claim 4, in which $R^3$ is 3,4-methylenedioxyphenyl.

6. A pharmaceutical composition comprising a compound as claimed in claim 1 and a pharmaceutically acceptable diluent or carrier.

7. A method of treating or preventing irritable bowel syndrome, diverticular disease, urinary incontinence, oesophageal achalasia, or chronic obstructive airways disease, comprising administering to a patient an effective amount of a compound according to claim 1.

* * * * *